US00PP37671P2

(12) United States Plant Patent
Byrne et al.

(10) Patent No.: US PP37,671 P2
(45) Date of Patent: Sep. 8, 2026

(54) PEACH TREE NAMED 'TX2C465CW'

(50) Latin Name: *Prunus persica*
Varietal Denomination: TX2C465CW

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,372

(22) Filed: Sep. 22, 2025

(51) Int. Cl.
*A01H 5/08* (2018.01)

(52) U.S. Cl.
USPC ..... Plt./195

(58) Field of Classification Search
USPC ..... Plt./156, 180, 194, 195
See application file for complete search history.

(56) References Cited

PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.
BYRNE and ANDERSON, 2013. White Delight peach series: Four medium-chill, subacid, white-fleshed peaches. HortScience 48(8): 1056-1058.
Rawandoozi, May 2019, QTL Mapping Through Pedigree-Based Analysis for Six Phenological and Quality Traits in Peach. Dissertation for Doctor of Philosophy. Texas A&M University.

*Primary Examiner* — Karen M Redden
(74) *Attorney, Agent, or Firm* — Dentons US LLP

(57) ABSTRACT

Disclosed is a new variety of *Prunus persica* named 'TX2C465CW'. This new variety, which requires approximately 550 chilling units of dormancy, is considered to be a peach tree of early season maturity, which produces subacid, non-melting, white-fleshed fruit that are very firm with a 70-90% medium to dark pink blush over a pale-yellow ground color, and suitable for fresh market use.

5 Drawing Sheets

Latin name of the genus and species of the plant claimed: *Prunus persica.*

Variety denomination: 'TX2C465CW'.

CROSS-REFERENCE TO RELATED APPLICATIONS

Peach trees developed under the same breeding program as 'TX2C465CW' include the co- pending applications listed below.

| U.S. application Ser. No. | Title |
|---|---|
| U.S. 19/336,141 | PEACH TREE NAMED 'TX3C490LWP' |
| U.S. 19/336,148 | PEACH TREE NAMED 'TRH2E68L' |
| U.S. 19/336,164 | PEACH TREE NAMED 'TRH3B53L' |
| U.S. 19/336,169 | PEACH TREE NAMED 'TRH3C114W' |
| U.S. 19/336,358 | PEACH TREE NAMED 'TRH2E121L' |
| U.S. 19/336,361 | PEACH TREE NAMED 'TRH3A17' |
| U.S. 19/336,363 | PEACH TREE NAMED 'TRH2E120LW' |
| U.S. 19/336,365 | PEACH TREE NAMED 'TRH3C113LW' |
| U.S. 19/336,368 | PEACH TREE NAMED 'TRH3E88LW' |
| U.S. 19/336,370 | PEACH TREE NAMED 'TX2B449LW' |
| U.S. 19/336,385 | PEACH TREE NAMED 'TRH2B102LW' |
| U.S. 19/336,375 | PEACH TREE NAMED 'TRH1C104LW' |
| U.S. 19/336,377 | PEACH TREE NAMED 'TRH3C111' |

-continued

| U.S. application Ser. No. | Title |
|---|---|
| U.S. 19/336,380 | PEACH TREE NAMED 'TRH2C108W' |
| U.S. 19/336,383 | PEACH TREE NAMED 'TRH2E116L' |

BACKGROUND OF THE INVENTION

This invention relates to a peach tree and, more specifically, to a peach tree referred to as a variety of *Prunus persica* named 'TX2C465CW', which requires approximately 550 chilling units of dormancy, produces a firm, non-melting, clingstone, white-fleshed, subacid peach with a 70-90% medium to dark pink blush over a pale-yellow ground color that matures early in the season. The present peach tree was the result of an ongoing Stone Fruit Breeding Program in College Station, Brazos County, Texas. To this end, controlled crosses were made each year to produce seedling populations from which improved progenies are evaluated and selected. 'TX2C465CW' was derived from a population created by crossing the high chill, white-fleshed, subacid peach 'White Delight Four' (not patented) with pollen of the medium-chill, subacid, yellow-fleshed, pantao nectarine 'Y435-250PF' (not patented). 'Y435-250PF' is a breeding selection with unknown parentage. Resulting seed from the 'White Delight Four' x 'Y435-250PF' hybrid family were planted in 2011 in an experimental plot in College Station, TX. 'TX2C465CW' was marked for subsequent observation in 2013 and noted as having exceptional characteristics.

'TX2C465CW' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Pleasanton (2018-2022), Somerville (2016-2024) and Fairfield (2016-2020), Texas. This evaluation clearly demonstrated that the re-propagated trees were true to the characteristics of the original seedling in all observable aspects.

SUMMARY OF THE INVENTION

The 'TX2C465CW' peach is characterized by producing clingstone, non-melting, white-fleshed, subacid fruit that ripens early in the season and produces a firm fruit with a 70-90% medium to dark pink blush over a pale-yellow ground color. In this regard, the present variety of peach tree bears fruit that is ripe for commercial harvesting and shipment in mid to late-May, when grown in the medium chill zone of Texas. 'TX2C465CW' blooms about 2 weeks before its female parent 'White Delight Four' (not patented, US App. Pub. No. 2016/0205831 P1, abandoned), and 3-4 days after its pollen parent the breeding selection Y435-250F (not patented). It ripens ~4 weeks before its female parent and ~2 weeks after its pollen parent. 'TX2C465CW' differs from its white-fleshed, subacid, peach female parent as it ripens 6 weeks before and requires 200 less chilling hours to fruit. It differs from its subacid, yellow-fleshed, nectarine, pantao pollen parent as it is a white-fleshed peach. It differs from both parents as it has non-melting flesh whereas its parents have melting flesh. This new subacid, white fleshed, peach differs from the two commercial subacid, white fleshed peaches ripening in the early to mid-season, 'White Delight One' (not patented, US App. Pub. No. 2016/0205833 P1, abandoned) and 'White Delight Two' (not patented, US App. Pub. No. 2016/0205832 P1, abandoned) in that it has non-melting flesh versus melting flesh. In addition, it has showy rather than non showy flowers, and ripens about 3 weeks after 'White Delight One' and about 10 days before 'White Delight Two'. This new subacid, white-fleshed, non-melting flesh, clingstone, early-ripening peach exhibits potential to be commercialized in regions that have chilling requirements that are moderately low.

BRIEF DESCRIPTION OF THE DRAWINGS

This new variety of peach tree is illustrated by the accompanying photographs of 3-year old to 5-year old plants grown in Fairfield, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
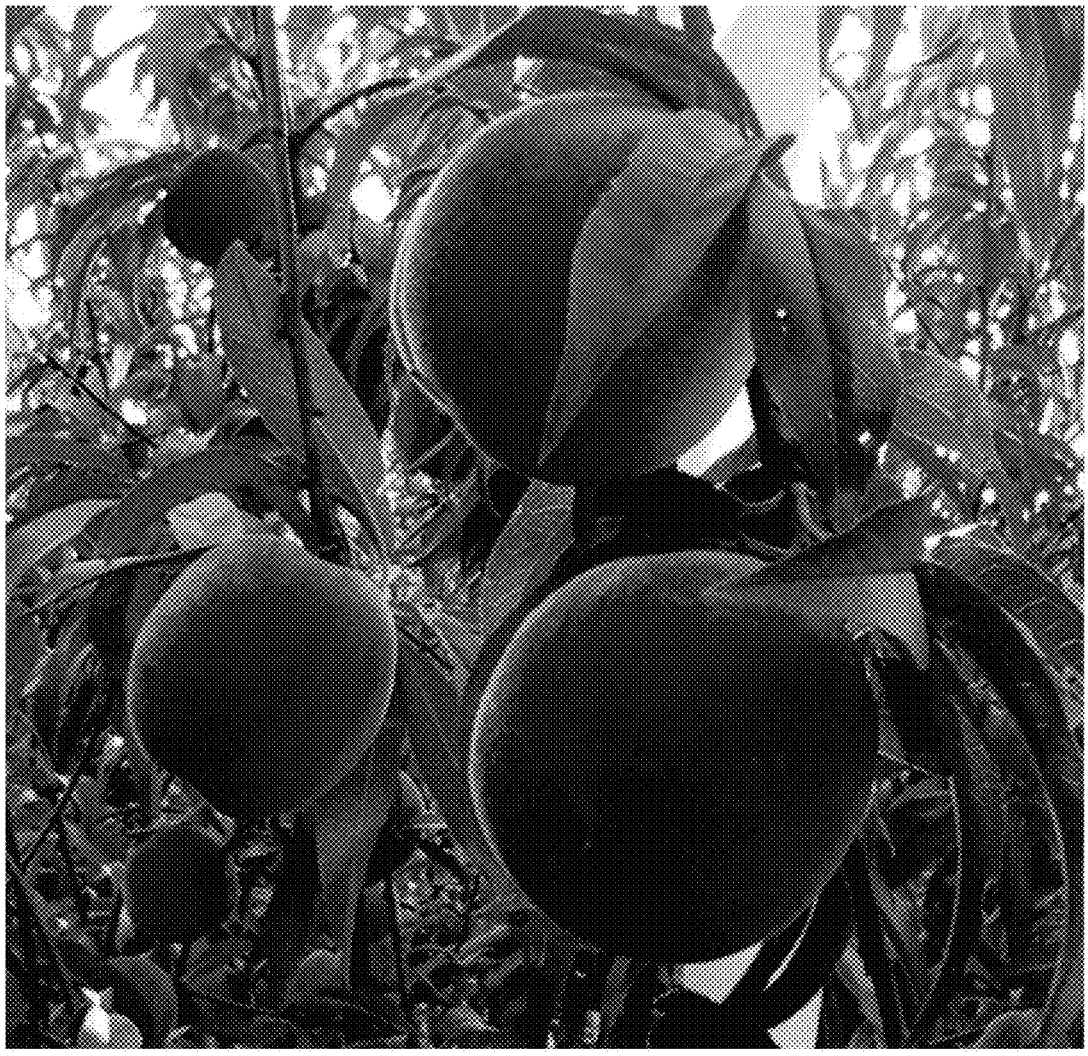
FIG. 1. Fruit of 'TX2C465CW' produced in Fairfield, Texas showing external and internal coloration.
Figure 2:
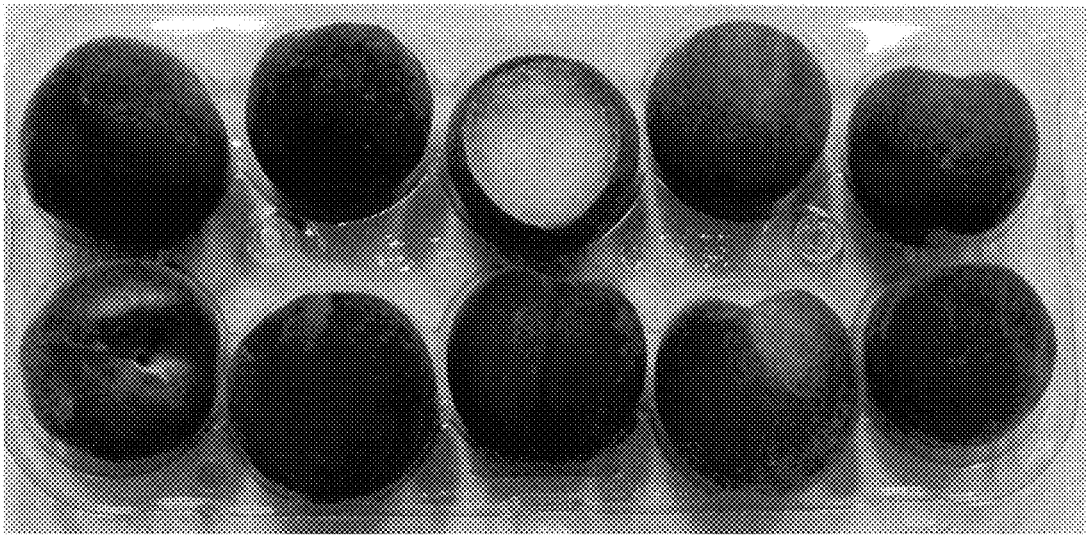
FIG. 2. 'TX2C465CW' fruit produced in Fairfield, Texas showing shape and external coloration.
Figure 3:
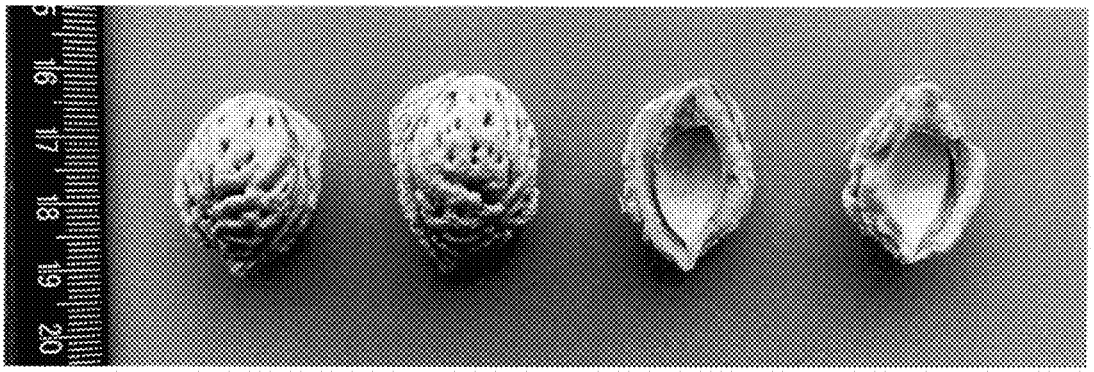
FIG. 3. Photograph of the endocarps of 'TX2C465CW' peach. The ruler is in centimeters.
Figure 4:
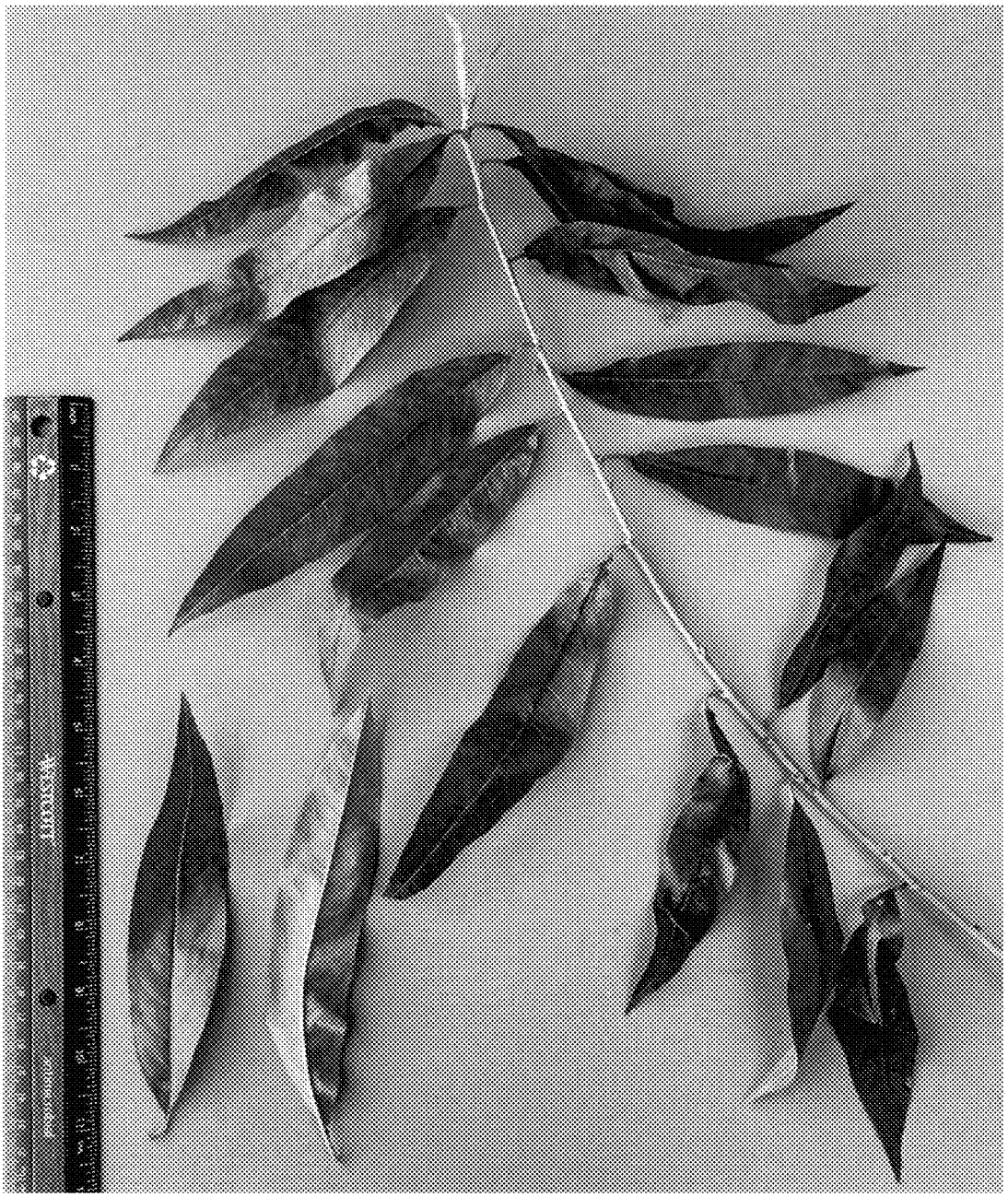
FIG. 4. A stem showing the leaves of 'TX2C465CW' peach. The ruler is in centimeters.
Figure 5:
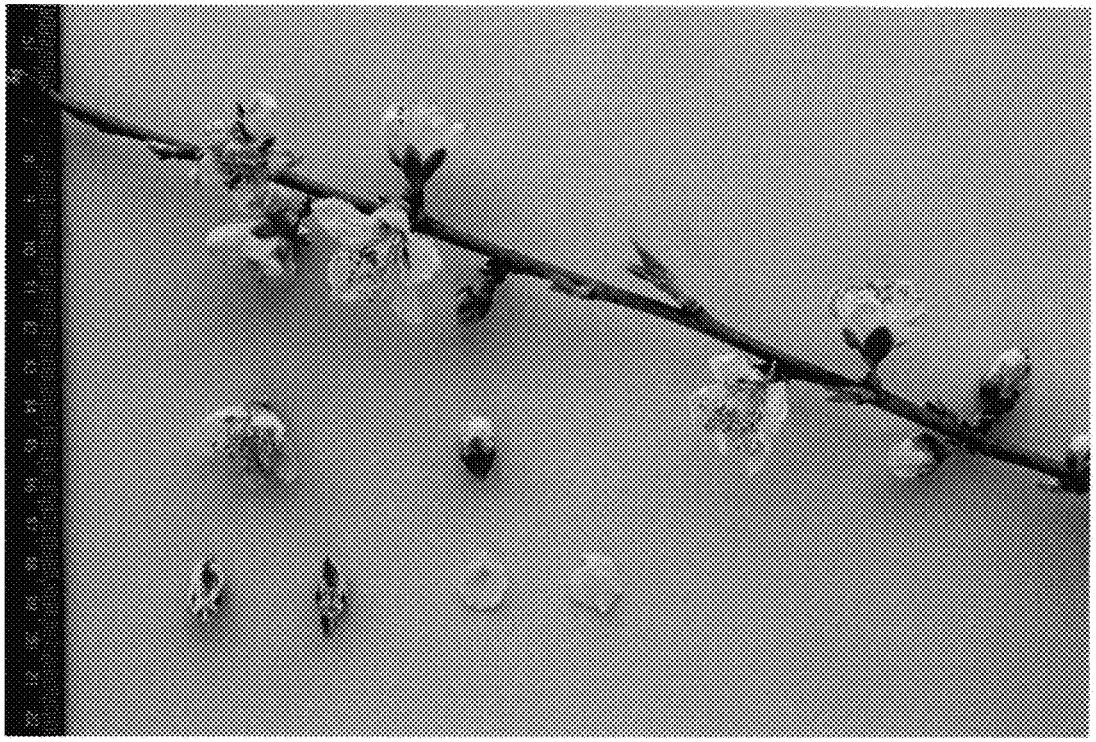
FIG. 5. A stem showing the flowers of 'TX2C465CW' peach. The ruler is in centimeters.

Referring more specifically to the pomological details of this new and distinct variety of peach tree, the following has been observed under the ecological conditions prevailing at the experimental orchards in the medium chill zone of Texas (Pleasanton, Fairfield, Somerville and College Station). All major color code designations are by reference to the R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average as compared to other common peach cultivars grown in the medium chill zone of Texas.

*Height*.—6 feet (1.8 m) at the end of the 2024 growing season.

*Width*.—9 feet width (2.7 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TX2C465CW' peach has been trained to an open center configuration but exhibits a low spreading growth type being more horizontal in growth than the semi-spreading peach varieties 'Texprince' (patented, U.S. Plant Pat. No. 14,629) and 'Texking' (patented, U.S. Plant Pat. No. 14,627).

*Current season growth*.—The current season growth for the new variety was approximately 1 to 3 feet (0.3-0.9 m). Vigor is medium compared to other common peach varieties grown in the medium chill zone of Texas.

*Regularity of bearing*.—Regular in the absence of temperatures of 28° F. or below during bloom and considered hardy in the medium chill zone of Texas.

Trunk:

*Size*.—Approximately 2.25 inches (5.7 cm) in diameter and 7.5 inches (19 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present.

*Bark coloration*.—Variable, colors (RHS 2001) present are 156A, 156B, 156C and 156D of the Greyed-White Group, 166A of the Greyed-Orange Group, N200D of the Brown Group, 201D of the Grey Group and 202D of the Black Group.

Branches:

*Thickness*.—About 3.3 cm in diameter as measured 10 cm from the trunk on a three-year old tree.

*Surface texture*.—Average and appearing furrowed on wood that is several years old.

*Lenticels*.—Numerous flat, oval lenticels present. The lenticels range in size from approximately 3 to 5 mm in width and were approximately 1.5 to 2 mm in height.

*Current season shoots*.—Surface texture — Substantially glabrous.

*Internode length*.—Approximately 1.6 to 2.5 cm as measured in the middle of a current season stem.

*Color of mature branches*.—The predominant colors (RHS2001) are 156D of the Greyed-White Group, 165A, 166A, 166B, 174A, 175A and 175B of the Greyed-Orange Group, 201D of the Grey Group and 202D of the Black Group.

*Current season shoots*.—Color (RHS2001) — Light to medium green, approximately 144A, 146C and 146D of the Yellow-Green Group, with some reddish-brown coloration appearing on exposed surface of the shoots 166A of the Greyed-Orange Group and 187A and 187B of the Greyed-Purple Group.

Leaves:

*Size*.—Considered moderately large to large for the species. Leaf measurements have been taken from vigorous upright current season growth approximately at mid-shoot.

*Leaf length*.—Approximately 169 to 198 mm.

*Leaf width*.—Approximately 34 to 39 mm.

*Leaf thickness*.—Less than 1 mm.

*Leaf form*.—Lanceolate.

*Leaf tip form*.—Acuminate.

*Leaf upper surface color* (*RHS*2001).—Green, 137B and 137C of the Green Group.

*Leaf lower surface color* (*RHS*2001).—Green, 137C of the Green Group and 146A and 146B of the Yellow-Green Group.

*Leaf lower mid-vein color* (*RHS*2001).—Light yellow green, 145C and 145D of the Yellow-Green Group.

*Leaf margins*.—Form — Considered crenate. Uniformity — Considered generally uniform.

*Leaf petioles*.—Length — Approximately 10 to 16 mm. Thickness — Approximately 2 mm. Color (RHS2001) — Pale green, 145C and 145D of the Yellow-Green Group. Texture — Glabrous.

*Leaf glands*.—Size — Approximately 1-1.5 mm in height and 1 mm in width. Number — Generally 2 per leaf. Type — Reniform. Color (RHS2001) — Greenish brown, 144A, N144C and N144D of the Yellow-Green Group.

*Leaf stipules*.—Length — Approximately 5 to 6 mm. Form — Lanceolate. Color (RHS2001) Abaxial/adaxial — Green, 144A and 146C of the Yellow-Green Group. The stipules are early deciduous. Ratio of flower to vegetative buds — Generally 2 flower buds per vegetative bud.

Flowers:

*Floral buds*.—General — The floral buds are conic in form, and slightly appressed relative to the bearing shoot. Color — The mature buds are brown (approximately 156A, 156B, 156C and 156D of the Greyed-White Group, 165A and 166A of the Greyed-Orange Group and 200B, 200C and 200D of the Brown Group). Mature Bud Length — Approximately 5 to 6 mm. Mature Bud Width — Approximately 2 mm.

*Blooming type*.—Mean date of full bloom in the medium chill zone of Texas was in late February to early March (average full bloom date was March 2$^{nd}$ at Somerville experimental plot), about 8-13 days after the commercial cultivars 'Texking' and 'Flordaking' (Andrews, 1979) and with 'Texstar' (Byrne and Kamas, 1984).

*Flower type*.—Showy.

*Flower size*.—Flower diameter at full bloom is approximately 30 to 33 mm.

*Bloom quantity*.—Considered abundant.

*Flower bud frequency*.—Normally 2 per node.

*Petal size*.—Width — Approximately 11 to 13 mm. Length — Approximately 17 to 18 mm.

*Petal form*.—Broadly ovate.

*Petal count*.—Generally 5-6.

*Petal color* (*RHS*2001) abaxial/adaxial.—Medium pink when young (62B, 62C, 62D, 65B, 65C and 69A of the Red-Purple Group), becoming darker near the petal claw.

*Petal claw*.—Form — The claw is considered truncate in shape. Length — Approximately 1 to 2 mm. Width — Approximately 1 mm.

*Petal margins*.—Generally considered variable, from nearly smooth to slightly undulate.

*Petal apex*.—Generally — The petal apices appear rounded.

*Flower pedicel*.—Length — Average length of 2 to 4 mm. Thickness — Approximately 1 mm. Color (RHS2001) — Light green (144C, N144D, 145A and 145B of the Yellow-Green Group).

*Floral nectaries*.—Color (RHS2001) — Light to medium yellow (3A, 3B, 5A, 5B, 5C, 6A, 6B, 6C, 8A, 8B, 9A, 9B, 9C, 12A and 12B of the Yellow Group).

*Sepals*.—

*Sepal number*.—Generally five per flower. Surface Texture — The surface has a short, fine, wooly texture. Size — Average Height 6.9 mm, Width 5.4 mm. Form — Ovate. Color (RHS2001) Abaxial — Maroon and green with white (approximately 58A, 59A, 59B, 59C and 60A of the Red-Purple Group; 138B of the Green Group; 144B, 144C, 144D and N144C of the Yellow-Green Group; 155A, 155B, 155C and 155D of the White Group and 183A, 183B, 183C, 184A, 184B, 185A, 185B, 187A, 187B and 187C of the Greyed-Purple Group).

*Floral cup* (*hypanthium*).—Surface Texture — Generally glabrous. Color (RHS2001) — Maroon with green (approximately 58A, 59A, 59B, 59C and 60A of the Red-Purple Group; 138B of the Green Group; 144B, 144C, 144D and N144C of the Yellow-Green Group and 183A, 183B, 183C, 184A, 184B, 185A, 185B, 187A, 187B and 187C of the Greyed-Purple Group).

*Anthers*.—Color (RHS2001) — Dark orange (approximately N34A of the Orange-Red Group). Pollen Production-Pollen is abundant and is a yellow color (approximately RHS2001 7A, 7B, 7C, 8A and 9C of the Yellow Group).

*Filaments*.—Size — Variable in length, approximately 11 to 16 mm, with the filaments being below or equal to the pistil height and the petal height at pink bud stage of development. Color (RHS2001) — White (approximately 155A, 155B, 155C and 155D of the White Group) and darkening with advanced maturity.

*Pistil*.—General — Taller or equal to the anther height and below or equal to the petal height. Length — Approximately 15 to 21 mm, including the ovary. Color (RHS2001) — Considered light yellow-green when young (approximately 1A, 1B, 1C and 1D of the Green-Yellow Group) and becoming slightly darker with advancing senescence.

*Surface texture*.—The variety has a long, silver white pubescent pistil (approximately RHS2001 1A, 1B, 1C and 1D of the White Group).

Fruit:

*Maturity when described*.—The present variety of fruit is described, as it would be found in its firm ripe condition at full commercial maturity. Under the ecological conditions prevailing in the medium chill zone of Texas it would be ripe in mid to late May. The average ripe date at Somerville is May 27$^{th}$ and in Fairfield would be May 18$^{th}$.

*Size*.—General — Medium for the season and considered uniform. Average Cheek Diameter — Approximately 55 to 63 mm. Average Suture Diameter — Approximately 57 to 63 mm. Average Axial Diameter — Approximately 50 to 56 mm.

*Fruit form*.—Generally considered oblate to round-ovate. Occasionally the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — The color of the suture is considered very dark pink (Red-Purple Group 59A and 59B, Purple Group N77A and Greyed-Purple Group 187A and 187B).

*Ventral surface*.—Form — Considered uniform.

*Stem cavity*.—Width — Approximately 18 to 20 mm. Length — Approximately 26 to 31 mm. Depth — Approximately 4 to 5 mm.

*Fruit base*.—Generally considered flat.

*Fruit apex*.—Generally considered flat.

*Fruit stem*.—Length — Approximately 10 mm. Thickness — Approximately 2 mm. Color (RHS2001) — Light green, 144D, N144D and 145B of the Yellow-Green Group.

*Fruit skin*.—Generally considered medium or average in thickness. Surface Texture — The variety has very short, thin pubescence. Skin Acidity — Considered neutral. Tenacious to Flesh — Yes at commercial maturity. Tendency to Crack — Cracking not observed. Skin Color — Generally-Variable, with approximately 70-90% of the fruit surface covered with a medium to dark pink blush. The fruit skin over color pattern varies from marbled to solid. Blush Color (RHS2001) — The medium to dark pink blush (Red Groups 46A and 53A, Red-Purple Group 59A and 59B and Greyed-Purple Groups 183A, 183B, 183C, N186C, 187A and 187B) has many degrees of shading and blending occurring between the stated colorations. Skin Ground Color (RHS2001) — The skin ground is a pale yellow (Yellow Groups 2D, 4C, 4D, 5D, 8C, 8D, 9D, 10C, 10D, 11D, 12D and 13D and Yellow-Orange Group 18C and 18D).

*Flesh color* (*RHS*2001).—Generally considered white (Yellow Group 11D and White Group 155B and 155D). Anthocyanin intensity in the flesh is generally medium to strong next to the skin, weak to medium centrally and weak next to the stone.

*Flesh fibers*.—Present throughout the flesh.

*Stone cavity color* (*RHS*2001).—Generally considered white (Yellow Group 11C and White Group 155B and 155D).

*Flesh texture*.—Generally, the flesh is on melting and very firm at commercial maturity.

*Ripening*.—Generally the fruit of the present variety ripens evenly.

*Flavor*.—Considered very sweet (average Brix 14.1) with subacid flavor.

Stone:

*Attachment*.—Clingstone at commercial maturity.

*Stone size*.—Length — Approximately 30 to 31 mm. Width — Approximately 22 to 23 mm. Thickness — Approximately 17 to 19 mm.

*Fibers*.—Generally fibers are attached along the entire surface of the stone.

*Stone form*.—Generally the stone is considered to be ovate.

*Stone base angle*.—The stone base is medium to wide.

*Hilum*.—Generally considered rather poorly defined as is common in early ripening varieties. The hilum is approximately 4 mm long and less than 1 mm wide.

*Stone apex angle*.—Medium.

*Stone shape*.—The stone shape is considered ovoid to elongated.

*Stone surface*.—Surface Texture — The surface texture consists of single pits, rosettes of pits and chains of pits. Ridges — Numerous fine ridges are present basally and converge towards the base of the stone.

*Ventral edge*.—Considered small to medium to large.

*Dorsal edge*.—Shape — Grooved with moderately rough edges.

*Stone color* (*RHS*2001).—The color of the dry stone is light to medium brown with no exact match of the RHS Colour Chart, but most similar to Greyed-Orange Groups 164C, 164D and 165D. The color of the inside surface of the endocarp is primarily Yellow-White Group 158A, Orange-White Group 159A and 159B, Greyed-Yellow Group 161C and 161D and Greyed-Orange Group 164D.

*Tendency to split*.—Splitting is relatively uncommon.

*Kernel*.—The kernel fills the endocarp at harvest and measures approximately 6 mm in thickness, 9-10 mm in width, and 15-16 mm in length. When dried the shriveled kernels measure approximately 2-4 mm in thickness, 9-10 mm in width, and 14-15 mm in length. The colors (RHS2001) of the fresh kernel are medium brown with dark brown venation (Greyed-Orange Groups 164B, 164C, 165A, 165B, 165C, Greyed-Brown Group N199C and N199D and Brown Group 200D).

*Use*.—The subject variety, 'TX2C465CW', is considered to be a medium chill peach tree of early-season maturity, which produces subacid, non-melting, white-fleshed fruit which are very firm, with a 70-90% medium to dark pink blush over a pale-yellow ground color and which are useful for fresh market use.

*Keeping quality*.—Average. Retains firmness and flavor after 14 days of refrigeration at 3-5° C.

*Resistance to insects and disease*.—No atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Pleasanton, Somerville, College Station and Fairfield, it will be understood that variations of the usual magnitude and characteristics incident to the changes in growing conditions, fertilization, pruning, 10 and pest control are to be expected.

What is claimed is:

1. A new and distinct variety of peach tree named 'TX2C465CW', as illustrated and described herein.

* * * * *